United States Patent [19]

Lerner

[11] Patent Number: 5,556,887
[45] Date of Patent: Sep. 17, 1996

[54] IMPROVED A PALMITATE COMPOSITION FOR TOPICAL APPLICATION WHICH ACHIEVES TO THE ENTIRE DERMAL MEMBRANE.

[76] Inventor: Sheldon Lerner, 3399 First Ave., San Diego, Calif. 92103

[21] Appl. No.: 432,529

[22] Filed: May 1, 1995

Related U.S. Application Data

[63] Continuation-in-part of Ser. No. 290,160, Aug. 15, 1994, Pat. No. 5,520,919.

[51] Int. Cl.$^6$ .................................................. A61K 7/48
[52] U.S. Cl. ...................... 514/772.6; 424/401; 514/844; 514/846; 514/847
[58] Field of Search ............................. 424/401; 514/725

[56] References Cited

U.S. PATENT DOCUMENTS

| | | | |
|---|---|---|---|
| 5,089,269 | 2/1992 | Noda et al. | 424/456 |
| 5,153,230 | 10/1992 | Jaffery | 514/847 |
| 5,243,021 | 9/1993 | Langer et al. | 528/272 |
| 5,380,764 | 1/1995 | Herzog | 514/725 |

*Primary Examiner*—Thurman K. Page
*Attorney, Agent, or Firm*—Linda Neyenesc

[57] ABSTRACT

A stable, non-oily, Vitamin A Palmitate composition having a high water ratio for dermatogical application to human skin. Non-irritating thickeners, preservatives and carriers synergize to achieve optimal bioavailability. A method of application of the composition achieves repair and rejuvenation of the entire dermal membrane.

1 Claim, No Drawings

IMPROVED A PALMITATE COMPOSITION FOR TOPICAL APPLICATION WHICH ACHIEVES TO THE ENTIRE DERMAL MEMBRANE.

PRIOR APPLICATION

This application is a continuation-in-part application of Ser. No. 08/290,160, filed Aug. 15, 1994 and now U.S. Pat. No. 5,520,919 and incorporates new material.

BACKGROUND OF THE INVENTION

1. Field of the Invention

The present invention relates to a stable Vitamin A palmitate composition and more particularly to a composition which excludes oils, contains a high ratio of water based surfactant, and means for topical application to human skin. More specifically, the present invention cures a wide range of skin disorders such as acne, uneven pigmentation, photoaging, excessive accumulation of epidermal layers and repair of the entire dermal tissue without irritating side effects.

PRIOR ART

2. Description of the Prior Art

U.S. Pat. Nos. 424,956 (Noda et al); 424,070 (Davis et al); 424,081 (Leong); 5,043,356 (Fulton, Jr.); 3,906,108 (Felty); 4,532,133 (Schmidt); 4,603,146 (Kligman) and 4,727,088 (Scott et al) have been reviewed for purposes of the prior art search.

A wide range of factors contribute to the phenotype of damaged skin. These factors may take the form of environmental toxins (smoke, pollution, etc.,), sun damage, genetic disposition, susceptibility of fair skin, and age. As stated by the reference to Fulton et al, the skin losses its ability to repair itself with age. Microscopic degradation becomes macroscopic, depending upon the combination of variables cited above which become manifested in early aging. These issues are non-disputed by the prior art patents.

Vitamin A is well known for its nutritional and therapeutic qualities, especially for the epithelia. Fulton discussed the internal use of Vitamin A palmitate in U.S. Pat. No. 5,043,356. Although his sources are not well documented, Fulton alleges stimulation of new cell growth in the epithelium only, with adverse side effects resultant from Vitamin A toxic symptoms. Fulton further alleges that topical application of the Vitamin A palmitate molecule is too large to transdermally traverse the necessary part of the skin. The site of the skin which Fulton alludes to is unstated, nor is there reference to the non-irritating effects of Vitamin A Palmitate as distinguished from other forms of Vitamin A. The instant invention overcomes Fulton in many respects.

To begin with, the topical application of the palmitate A solution does not cause any known adverse side effects. Therefore, it can be administered freely and safely without burning the skin. Side effects associated with early research of internally administered A Palmitate (1940), such as headaches, migraine headaches, fatigue, bone pain, etc., further distinguish the instant invention. Topical treatment is an entirely different application. Yet another limitation of the A Palmitate experiments cited by Fulton may have been utilization of insufficient amounts of A palmitate.

Applicants composition overcomes yet another reference to Noda et al, U.S. Pat. No. 424,456. To begin with, Noda's preferred embodiment is a "water-in-oil" type emulsion". Although water is utilized by Noda, all of his compositions contain high percentages of oil. Topical application of oil clogs the pores of human skin and therefore prevents penetration to the dermis and collagen layer. Applicant's composition is distinctive over the fatally flawed Noda reference in view of its high water ratio, non-irritating effects of the A Palmitate type of Vitamin A, and superior absorption qualities. Although absent in the Noda reference, Aloe Vera is the only substance which could be characterized as partly oil. Applicant has purposefully included this substance in his composition because it is extremely unique in that it contains resin, emodin and volatile oil. Aloe Vera yields not less than 50% of water soluble extractive. *The Merck Index, Eleventh Edition,* page 307 at "302". Noda is consistent with oily properties throughout his patent, especially by defatting and washing (Column 2, lines 6–15). Noda's compositions and methods are distinctive from applicant's novelty which sets forth a technique of cleansing and defatting the skin before application of the A Palmitate composition. The recitations of Noda's composition, i.e., Column 8, line 54, further teach the use of copious amounts of oil on the following page under Column 9. As to Column 29, lines 42–60 and 67–68 and Column 30, lines 1–6, Noda utilizes not only oil, but microcrystalline wax, beeswax and liquid paraffin, all subtances that clog the pores of human skin and distinguish applicant's composition over Noda et al, or any reference heretofore cited. Even if Noda were to utilize Aloe Vera in his composition, he could not possibly achieve the superior penetration qualities of the A Palmitate composition because of the plethora of substances set forth above which clog the carrier mechanism of water and this is a pivotal distinction which overcomes the Noda reference. Noda is therefore fatally flawed.

Yet another reference to Leong (424,081) utilizes Aloe Vera. Leong in combination with Noda could not achieve applicant's invention because of the numerous pore-clogging substances of Noda. No amount of the volatile Aloe Vera could overcome the penetration problems of Noda due to Noda's oily substances, in combination with beeswax, microcrystalline wax and paraffin. Therefore, this combination is unobvious.

Yet another reference to Davis (424,070) disclaims the use of the retinol palmitate in claim 1. Davis demonstrates that different types of the Vitamin A composition exhibit varying types of irritancy properties. Davis utilizes Vitamin A Propionate on hair, a totally different type of tissue, i.e., a dead epithelial cell lacking a stratified cornified epithelium at the surface and distal to the dermis and collagen layers which are the main focus of applicant's novelty. Although discussed in Davis, irritancy properties are not relevant to the dead epithelial cell of hair.

There is mounting evidence borne out by recent research and the instant inventor's reduction to practice of his composition and method of application that the molecules transcend the stratified epithelium to access the dermis. Not only does the composition exfoliate dead cornified layers, it reaches the mesenchyme, allowing repair, thickening, and proliferation of new cell layers as well as increased blood flow. Basal improvements are manifested in the epithelium which then becomes smoother and less pigmented. The method of achieving these results will be more fully described.

Schmidt (U.S. Pat. No. 4,532,133) discusses the instability of the Vitamin A molecule when exposed to air oxidation, heat and/or water prior to the addition to animal feed. Applicant's composition is hermetically sealed and is applicable to human use vis-a vis animal feed, a significant improvement over the Schmidt patent.

The patent to Kligman (4,603,146) utilizes a composition of Vitamin A acid (retionic acid). The patent describes a carefully monitored sub-irritating dose of the potentially harmful retionic acid. The instant invention overcomes Kligman on at least two points. Although Kligman discusses Vitamin A (acid) in an emollient vehicle, the dosage must be carefully monitored because of the harmful effects of this form of acid on the skin. The Palmitate A composition of the instant invention overcomes Kligman because it does not irritate the skin, even in its highest concentration. Nor does Kligman state in his singular main claim the proportions of A acid to emollient. He merely states that the dosage be sub-irritating. The method, means, maintenance therapy and composition are therefore extremely ambiguous if not totally absent from the invention as claimed.

Scott (U.S. Pat. No. 4,727,088) comprises a pharmaceutical preparation in the form of an antiperspirant stick in combination with a volatile alcohol and the retinoid acid form of Vitamin A for the treatment of ache. The limitations of the sub-irritating dosage problems have been discussed above, especially with respect to the Kligman patent. Felty (U.S. Pat. No. 3,906,108) also utilizes the potentially harmful retinoid acid in yet another emulsion (xanthan gum, et al) for purposes of enhanced shelf-life and stability.

Until the emergence of the present invention, there has been no safe and effective means of treating skin disorders and aging with topical application.

SUMMARY OF THE INVENTION

This invention is directed to the treatment of physiologic conditions commonly associated with aging of human skin and more particularly a composition which excludes oily properties, an improvement over the prior art. These morphological symptoms include visible wrinkles, leatheriness, roughness, dryness, skin looseness, loss of elasticity, pronounced pigment variations and lesions. Accompanying these symptoms are reduced cell development and exfoliation with a thickened epidermal layer. The foregoing conditions are mirrored in the condition of the underlying dermis. The supporting fascicular and soluble collagen and elastin fibers lose support for the epidermis. Mechanical and nutritive support for the epidermis thus diminishes.

The invention is based upon the discovery that sufficient amounts of Vitamin A Palmitate in combination with a specific composition achieves bioavailability of the A molecule in the dermis and epidermis. The novelty is achieved by superior absorption qualities in the form of a high ratio deionized water in combination with Aloe Vera, a volatile oil. These two factors synergize to effect the most effective penetration Besides the superior penetration qualities of the A composition, there is also mounting evidence that the stratified epidermis displays a coordinated response from a proliferating basal cell to the mature, upper layers. These growth factor signaling pathways are generated low in the basal layer and induce a molecular signal for cell proliferation throughout the companion dermal tissue. Years of research by the instant inventor have culminated in a product that accesses the dermis in combination with a synergism of appropriate carrier's of the A molecule and the physiological mechanism of molecular signaling. This synergism is readily apparent when the skin is viewed as a viable and dynamic organ, interacting as a whole. An additional aspect of the present invention is the absence of irritating side effects which make possible a more liberal method of topical application and enhanced repair time of skin tissue.

DETAILED DESCRIPTION OF THE INVENTION

The therapeutic component of the Vitamin A Palmitate molecule is distinguished from other derivatives of Vitamin A, as follows:

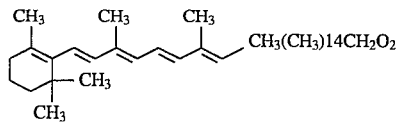

The limitations of topical treatment with other forms of Vitamin A have been discussed in the prior art portion of this application. The following description sets forth the substantial improvement over the prior art and its effectiveness in harnessing Vitamin A Palmitate, the safest and most effective modulator of growth and regeneration.

Without limiting the scope of the invention and for purposes of illustration, the aqueous base composition of the present invention for application to human skin is described as follows. Vitamin A Palmitate is carried by a water surfactant in the approximate solution of 51% (preferably deionized water). The percentage of A Palmitate to water has been found effective in the range of 4–10% In contrast to other carriers in the prior art which bind the A molecule and reduce its bioavailability, the water and Aloe Vera evaporate, thus allowing the Vitamin A its maximum exposure to access the dermal layers. The water slurry also contains carboxyvinyl polymers, polyoxyethlene and sorbitan sesquioleate. In combination, these inert substances provide a non-irritating suspension. A small but significant percentage of Aloe Vera synergizes with the deionized water surfactant to achieve an extremely efficient carrier of the A Palmitate inasmuch as both substances easily penetrate the dermis and likewise evaporate to achieve penetration into the skin but leaving the A Palmitate in situ.

Stabilization is achieved by inclusion of the preservatives selected from the group of phenoxyethanol, methylparaben, proplparaben.

Without limiting the scope of the invention, the preferred method of preparing the stable composition follows:

To 60 grams of deionized water, add 30 grams of carboxyvinyl polymers in a 1.5 wt/% solution;

add five grams of polyoxyethylene;

heat to 160 F;

to the above composition add six grams of Vitamin A palmitate, two grams sorbitan sesquioleate, 0.5 grams of urea, inositol, sodium lactate, sodium PCA padimate, niacinamide, phenoxyethanol, lactic acid, methylparaben, propylparaben and 0.1 grams of BHT, sodium benzoate and citric acid;

mix the solution while cooling to 110 F and add 5 grams if aloe vera; and mix the viscosity to 25,000 cPs using a viscometer and add a 10% solution of sodium hydroxide.

Topical application of the A Palmitate composition achieves rejuvenation and healing of the total dermal organ without adverse side effects. As stated hereinbefore, undesirable skin conditions take the form of acne, damaged basal membranes, excessive accumulation of epidermal layers, photoaging, and uneven pigmentation. The pathology of skin disorders is infinite; however, the instant invention has reduced to practice a composition and method which cure and/or mitigate a large number of them. The results are exhibited by exfoliation of dead, cornified layers, access to the basal tissue, repair, thickening and proliferation of new cell layers, as well as increased blood flow. Morphological improvement has been observed in the young, proliferating dermis and there is clear evidence that the instant composition displays evidence of accessing the basal layer by means of its superior penetration qualities in combination with stimulation of growth factor signaling pathways within the total epithelia.

The composition has proved equally effective with varying skin types of pigment and oil production. Because of its non-irritating qualities, the application does not comprise a pharmaceutical substance which requires monitoring or prescription. The human research subjects used the composition liberally and none of the irritating side effects of Vitamin A acid were observed. The percentages in the data of low improvement indicated improper application procedures. These experiments are current and inprogress.

EXAMPLE 1

Preparation of a Water Based Composition in Combination with Vitamin A Palmitate for Treating Skin Disorders One hundred patients between the ages of thirty-five and sixty applied the A Palmitate composition in the solution described for a period of six months. Applications were made once daily following a cleansing and defatting of the skin. At the end of three months 82% showed noticeable improvement in overall skin conditions. These improvements included a reduction in hyperpigmentation, improved clarity and firmer skin tone.

At the end of six months 91% showed improvement in overall skin conditions, and the majority of subjects exhibited significant improvement in skin firmness and reduction of noticeable lines and wrinkles. The remainder of patients showing little improvement indicated deviation from the research protocol.

EXAMPLE 2

Preparation of a Water Based Composition in combination with Vitamin A Palmitate for Treating Skin Disorders Fifty patients between the ages of thirty-five and sixty applied the A Palmitate Composition in the solution described and applications of at least 4% glycolic cleanser, 15% glycolic toner and 10% glycolic lotions. Applications of the A Palmitate Composition were made once daily in the morning following cleansing and defatting of the skin; applications of the glycolic products were made once daily in the evening.

At the end of three months 86% exhibited noticeable improvement in overall skin conditions. These improvements included reduction in hyperpigmentation, improved clarity and firmer skin tone. Patients in this group exhibited significant mitigation of hyperpigmentation than the control group of Example 1.

At the end of six months 93% manifested clear clinical evidence of improvement in overall skin conditions and the majority of subjects showed marked improvement in firmness, reduction of noticeable lines, and wrinkles. Firmness and mitigation of lines was more noticeable than in Example 1 and skin clarity was greatly enhanced. The remaining 7% indicated deviation from the experiment protocol.

EXAMPLE 3

Preparation of a Water Based Composition in Combination with Glycolic Cleanser, Toner and Lotion for Treatment of Skin Disorders Fifty patients between the ages of thirty-five and sixty applied 4% glycolic cleanser, 15% glycolic toner and 10% glycolic lotion for a period of six months. Applications were made once daily. At the end of three months, 86% exhibited improvements in skin conditions; however, the majority had improvement in hyperpigmentation only.

At the end of six months 88% showed overall improvement of skin conditions. Improvement in hyperpigmentation was equal to Examples 1 and 2. Improvement in noticeable lines and wrinkles was less than Examples 1 and 2. Improvement in skin firmness occurred in few patients and could be attributed to a general improvement in skin care practices.

As can be seen from the above examples, the preferred embodiments are set forth in Examples 1 and 2 which yield superior results and higher percentages of clinical success (93%). It was also discovered that six months of daily applications accomplished the highest improvement rate.

Example 3 has been included for purposes of omitting the A Palmitate composition and, although there was noticeable improvement, Examples 1 and 2 clearly establish the effectiveness of the Palmitate A topical treatment.

While there have been shown and described the preferred embodiment of the Palmitate A composition and its application, it will be appreciated that changes and alterations may be made therein without departing from the spirit and scope of the essential spirit of the invention.

What is claimed is:

1. A method for the preparation of a composition for topical application comprising the following procedure:

to 60 grams of deionized water, add 30 grams of carboxyvinyl polymers in a 1.5% solution;

add five grams of polyoxyethylene;

heat to 160 F;

to the above composition add six grams of Vitamin A Palmitate, two grams of sorbitan sesquioleate, 0.5 grams of urea, inositol, sodium lactate, sodium PCA padimate, niacinamide, phenoxyethanol, lactic acid, methylparaben, propylparaben and 0.1 grams of BHT, sodium benzoate and citric acid;

mix the solution while cooling to 100 F and add five grams of Aloe Vera; and mix the viscosity to 25,000 cPs using a viscometer an add a 10% solution of sodium hydroxide.

* * * * *